United States Patent

Moon et al.

Patent Number: 5,817,858
Date of Patent: Oct. 6, 1998

[54] CARBAMATE COMPOUNDS HAVING N-SUBSTITUTED THIOCARBAMOYL GROUP AND PROCESS FOR PREPARING THE SAME

[75] Inventors: Choi Yong Moon, Towaco, N.J.; Han Dong Il; Kim Hyung Cheol, both of Taejon, Rep. of Korea

[73] Assignee: Yukong Limited, Seoul, Rep. of Korea

[21] Appl. No.: 629,619

[22] Filed: Apr. 9, 1996

[30] Foreign Application Priority Data

Apr. 10, 1995 [KR] Rep. of Korea .................... 1995 8309

[51] Int. Cl.[6] ................................................. C07C 333/02
[52] U.S. Cl. .............................................................. 558/234
[58] Field of Search ..................................... 558/234, 233

Primary Examiner—Johann Richter
Assistant Examiner—Michael G. Ambrose
Attorney, Agent, or Firm—Abelman, Frayne & Schwab

[57] ABSTRACT

There is disclosed 3-N-substituted thiocarbamoyl-2-phenyl-1,3-propanediol carbamate, represented by the following structural formula I, that is very effective for prophylaxis and treatment of central nervous system disorders including nervous muscular pain, epilepsy and cerebral apoplexy:

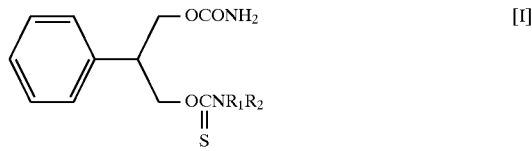

wherein $R_1$ and $R_2$ may be the same or different from each other and are independently selected from the group consisting of hydrogen, lower alkyl containing 1 to 8 carbon atoms and 5 to 7-membered aliphatic cyclic compound which may comprise two or less nitrogen or oxygen atoms directly unconnected, with a proviso that $R_1$ and $R_2$ both should not be hydrogen and the total number of carbon atoms of $R_1$ and $R_2$ ranges from 1 to 16.

22 Claims, No Drawings

CARBAMATE COMPOUNDS HAVING N-SUBSTITUTED THIOCARBAMOYL GROUP AND PROCESS FOR PREPARING THE SAME

BACKGROUND OF THE INVENTION

1Field of the Invention

The present invention relates to novel carbamate compounds derived from 2-phenyl-1,3-propanediol monocarbamates. More particularly, the present invention relates to 3-N-substituted thiocarbamoyl-2-phenyl-1,3-propanediol carbamate useful to treat the, diseases of the central nervous system. Also the present invention is concerned with methods for preparing the same.

2. Description of the Prior Art

Carbamates have been effectively used for controlling central nervous system (hereinafter referred to as "CNS") disorders, especially, as antiepileptics and centrally acting muscle relaxants. For example, 2-methyl-2-propyl-1,3-propanediol dicarbamate was reported in J. Am. Chem. Soc., 73, 5779 (1951), and the pharmaceutical activity thereof was ascertained in J. Pharmacol. Exp., Ther., 104, 229 (1952).

U.S. Pat. No. 2,884,444 discloses 2-phenyl-1,3-propanediol dicarbamate and U.S. Pat. No. 2,937,119 discloses isopropyl meprobamate. These carbamate compounds are found to be very effective therapeutic medicines against CNS disorders, in particular, as an antiepileptic and a centrally acting muscle relaxant, respectively.

Active research and development efforts have been and continues to be directed to the application of carbamates for CNS disorders.

SUMMARY OF THE INVENTION

As a result of intensive and thorough research for the derivatives of 2-phenyl-1,3-propanediol monocarbamates, the present inventors found that thiocarbamoyl-introduced carbamates are pharmaceutically very useful in prophylaxis and treatment of CNS disorders, for example, epilepsy, cerebral apoplexy and: nervous myalgia.

Accordingly, it is a principal object of the present invention to provide novel N-substituted thiocarbamoyl compounds effective for prophylaxis and treatment of CNS disorders.

It is another object of the present invention to provide a method for preparing the novel N-substituted thiocarbamoyl compounds.

DETAILED DESCRIPTION OF THE INVENTION

In accordance with an aspect of the present invention, there are provided novel carbamate derivatives that are pharmacologically superior in prophylaxis and treatment of CNS disorders, represented by the following structural formula I:

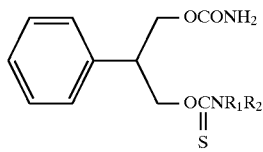

wherein $R_1$ and $R_2$ may be the same or different from each other and are independently selected from the group consisting of hydrogen, lower alkyl containing 1 to 8 carbon atoms, and 5 to 7-membered aliphatic cyclic compounds which may comprise two or less nitrogen or oxygen atoms directly unconnected, with a-proviso that $R_1$ and $R_2$ both should not be hydrogen and the total number of carbon atom of $R_1$ and $R_2$ ranges from 1 to 16.

In accordance with another aspect of the present invention, there are provided novel carbamate derivatives that are pharmacologically superior in prophylaxis and treatment of CNS disorders, represented by the following structural formula I';

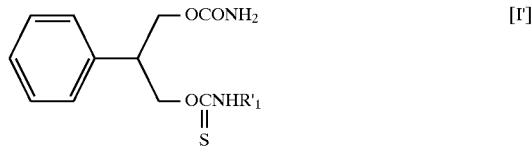

wherein $R'_1$ is alkyloxy carbonyl containing 1 to 8 carbon atoms or aryl containing benzene ring.

In accordance with the present invention, the compound of structural formula I can be prepared as follows:

2-phenyl-1,3 -propanediol monocarbamate, represented by the following structural formula II:

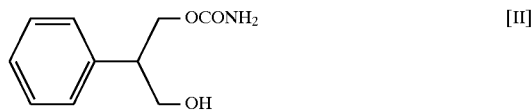

is first reacted with sodium hydride and carbon disulfide in a solvent. Without separation, the reaction solution is treated with alkyl iodide represented by the following. structural formula IV:

$$R_3I \qquad [IV]$$

wherein $R_3$ is a lower-alkyl containing 1 to 3 carbon atoms, such an methyl, ethyl and propyl, with preference to methyl, to synthesize 3-(alkyldithiocarbonyl-2-phenyl-1,3-propanediol carbamate, represented by the following structural formula III:

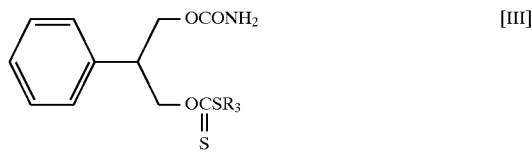

wherein $R_3$ is as defined above. Then, this carbamate is reacted with an amine, represented by the following structural formula V:

$$HNR_1R_2 \qquad [V]$$

wherein $R_1$ and $R_2$ may be the same or different from each other and are independently selected from the group consisting of hydrogen, lower alkyl containing 1 to 8 carbon atoms, and 5 to 7membered aliphatic cyclic compound which may comprise two or less nitrogen or oxygen atoms directly unconnected with a proviso that $R_1$ and $R_2$ both should not be hydrogen and the total number of carbon atoms of $R_1$ and ranges from 1 to 16, to give 3-N-substituted thiocarbamoyl2-phenyl-1,3-propanediol carbamate, represented by the following structural formula I:

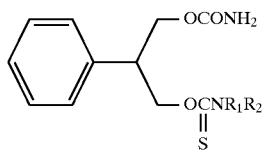

[I]

wherein $R_1$ and $R_2$ are as defined above.

This pathway is summarized in the following reaction scheme:

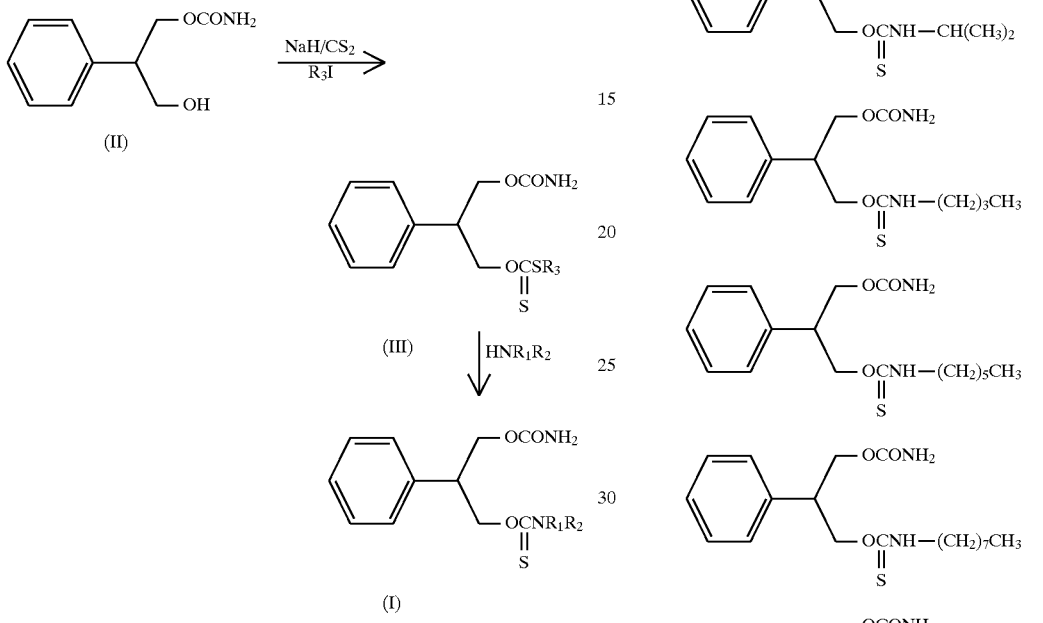

In more-detail, about 0.1 to 3.0 moles of the compound of structural formula II, the starting material, is added with about 1.0 to 2equivalents of sodium hydride and carbon disulfide each. This reaction system also comprises the alkyl iodide at an amount of about 1.0 to 2.5 equivalents. The synthesis reaction of compound III from compound II is carried out at temperatures of −10° to 30° C. The examples of solvent used in this reaction include amides such as dimethylformamide, sulfoxides such as dimethyl sulfoxide, and others such as ethyl ether and tetrahydrofuran, with preference to ethyl ether and tetrahydrofuran. When preparing compound I from compound III, the amine is added at an amount of about 1.0 to 5.0 equivalents. This reaction is preferably carried out at temperatures ranging from −10° to 30° C. in an ethereal solvent such as tetrahydrofuran.

The following compounds, not limitative but illustrative, are those that can be synthesized by the above-mentioned method.

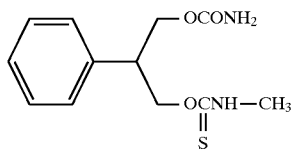

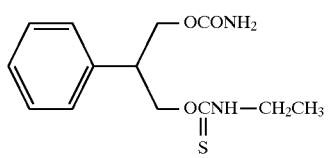

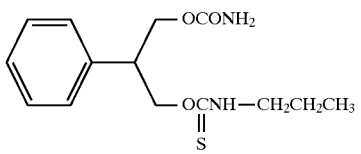

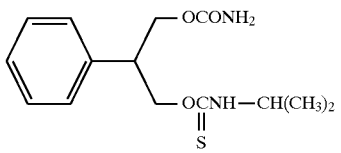

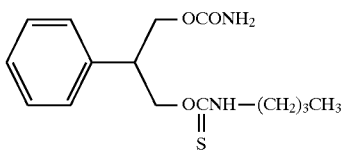

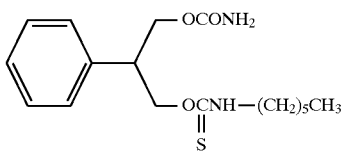

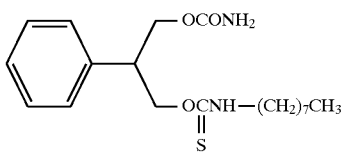

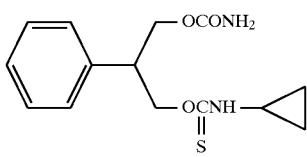

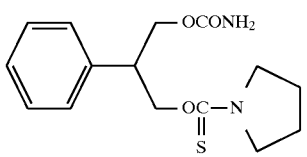

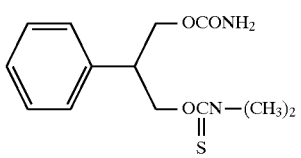

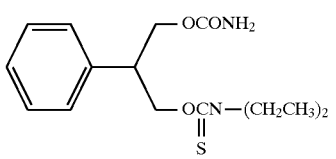

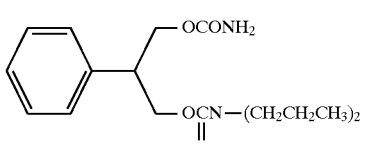

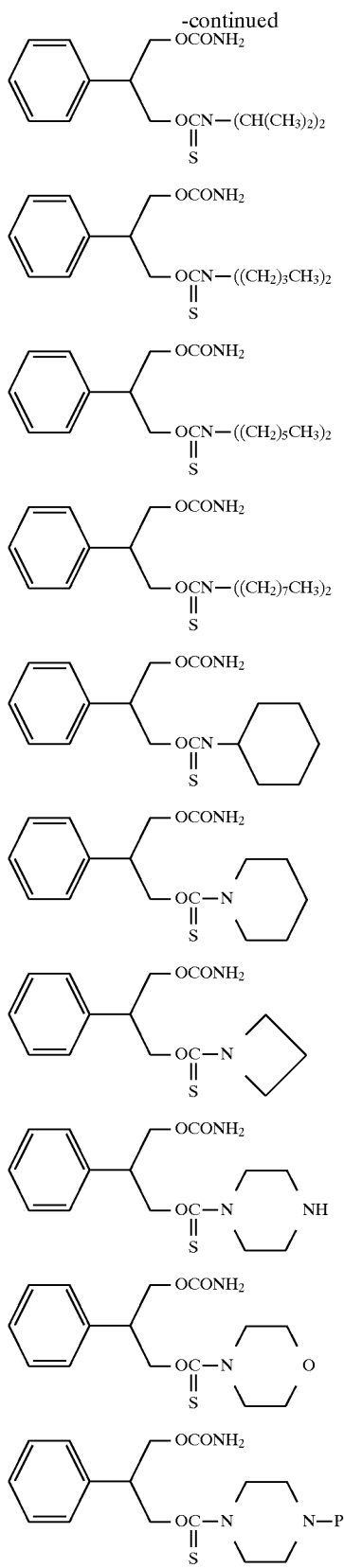

The following is the method for preparing the compound I' of the present invention.

The compound represented by the structural formula II, is reacted with isothiocyanate represented by the following structural formula VI:

$$R'_1NCS \qquad [VI]$$

wherein $R'_1$ means an alkyloxy carbonyl containing 1 to 8 carbon atoms or an aryl containing benzene ring, in a solvent, to give 3-N-substituted thiocarbamoyl-2-phenyl-1,3-propanediol carbamate, represented by the following structural formula I':

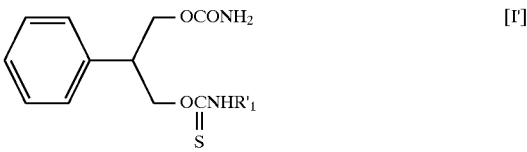

wherein $R'_1$ is an alkyloxy carbonyl containing 1 to 8 carbon atoms or an aryl containing benzene ring.

This pathway is summarized in the following reaction scheme:

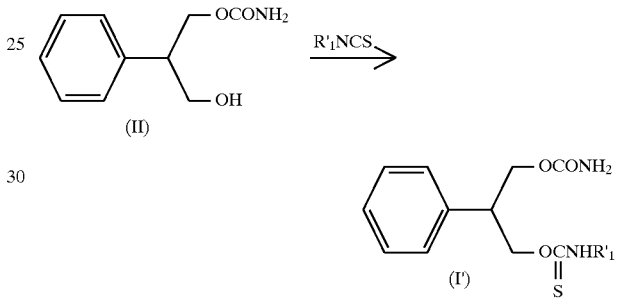

In the above method, about 0.1 to 3.0 moles of compound II are used along with about 1.0 to 2.0 equivalents of isothiocyanate. This reaction is carried out at temperatures ranging from 30° to 110° C. As a solvent, a halogenated hydrocarbon such as dichloromethane and chloroform, an ethereal solvent such as ethyl ether and tetrahydrofuran, or an aromatic hydrocarbon such as benzene is available with preference to dichloromethane or chloroform.

The following compounds, not limitative but illustrative, are those that can be prepared through the above method.

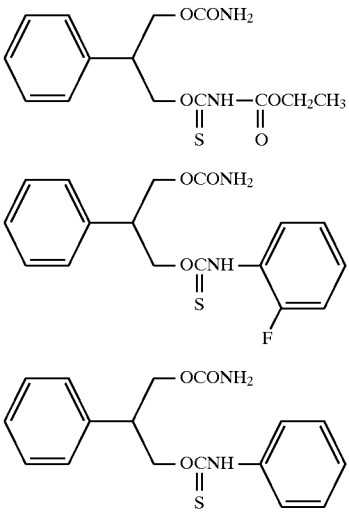

-continued

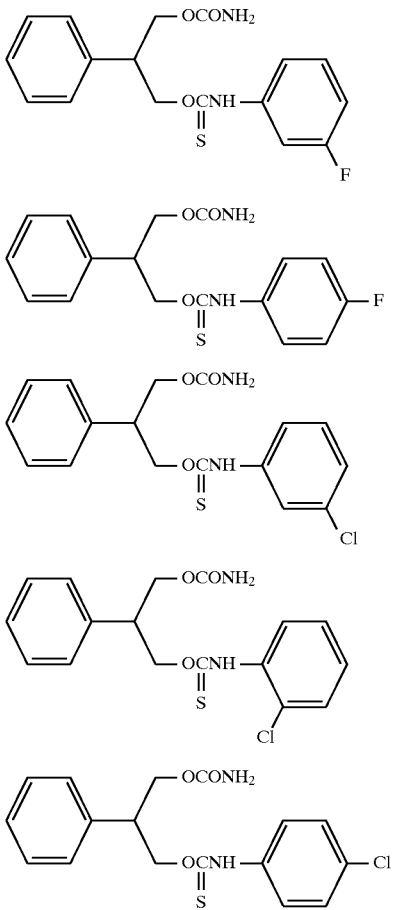

A better understanding of the present invention may be obtained in light of following examples which are set forth to illustrate, but are not to be construed to limit, the present invention.

EXAMPLE I
Preparation of 3-O-(N-methyl)dithiocarbonyl-2-phenyl-1,3-propanediol carbamate 1000 ml flask equipped with a thermometer was well dried and purged by flowing nitrogen gas into the inside thereof to remove moisture and air which might be present therein, and maintained at 0° C. using an ice bath. After 30 min., 10 g of 2-phenyl-1,3-propanediol monocarbamate was dissolved in 250 ml of tetrahydrofuran purified with sodium metal and benzophenone and placed in the flask. A homogeneous solution was made by stirring for 30 min.

While being maintained at 0° C., the homogeneous solution was slowly added with 1.4 g of sodium hydride and stirred for 60 min, after which 3.6 ml of carbon disulfide was slowly added using a syringe.

At about 60 min. after the addition of carbon disulfide, thin layer chromatography revealed that all of the starting material disappeared. Reaction was further proceeded by addition of 3.8 ml of methyl iodide while maintaining the reaction solution at 0° C. The progress of the reaction was monitored by thin layer chromatography and liquid chromatography. It took about 2 hours to determine the reaction termination.

Thereafter, the resulting reaction mixture was added with 300 ml of distilled water and 200 ml of ethyl other, for the purpose of solvent extraction. The organic layer thus obtained was dried over anhydrous magnesium sulfate and the solvent was completely evaporated by a rotary evaporator, to give yellow liquid. This residue was subjected to column chromatography (mobile phase, ethylacetate:n-hexane=1:2) to give 11 g of 3-O-(N-methyl)dithiocarbonyl-2-phenyl-1,3-propanediol carbamate: Yield 78%.

$^1$H-NMR(CDCl$_3$, 200 MHz); ppm ($\delta$):
2.45–2.50(s,3H), 3.45–3.60(q,1H), 4.34–4.39(d,2H), 4.77–4.83(d,2H), 4.86–5.15(br,2H), 7.21–7.39(m,5H)

EXAMPLE II
Preparation of 3-O-(N-methyl)thiocarbamoyl-2-phenyl-1,3-propanediol carbamate 1000 ml flask equipped with a thermometer was well dried and purged by flowing-nitrogen gas into the inside thereof to remove moisture and air which might be present therein, and maintained at 0° C. using an ice bath. After 30 min., 5.7 g of 3-O-(N-methyl)dithiocarbonyl-2-phenyl-1,3-propanediol carbamate obtained in Example I was dissolved in 200 ml of tetrahydrofuran purified with sodium metal and benzophenone and placed in the flask. A homogeneous solution was made by stirring for 30 min.

While being maintained at 0° C., the homogeneous solution was slowly added with 4.7 ml of 40% methylamine solution in water.

At about 60 min. after the addition of the aqueous methyl amine solution, the ice bath was removed to proceed the reaction at room temperature. The progress of the reaction was monitored by thin layer chromatography and liquid chromatography. It took about 2 hours to determine the reaction termination.

Thereafter, the resulting reaction mixture was added with 100 ml of distilled water and 100 ml of ethyl ether, for the purpose of solvent extraction. The organic layer thus obtained was dried over anhydrous magnesium sulfate and the solvent was completely evaporated by a rotary evaporator, to give yellow liquid. This concentrated residue was subjected to column chromatography (mobile phase, ethylacetate:n-hexane=1:1) to obtain 5.1 g of 3-O-(N-methyl)thiocarbamoyl-2-phenyl-1,3-propanediolcarbamate: Yield 95%.

$^1$H-NMR(CDCl$_3$, 200 MHz), ppm ($\delta$):
2.73–2.78(d,1H), 2.96–3.09(d,2H), 3.32–3.55(m,1H), 4.25–4.39(m,2H), 4.62–4.92(br,2H), 6.41–6.56 (br,1H), 6.92–7.05(br,1H), 7.10–7.38(m,5H)

EXAMPLE III
Preparation of 3-O-(N,N-dimethyl)thiocarbamoyl-2-phenyl-1,3-propanediol carbamate The procedure of Example II was repeated using 6.8 ml of dimethyl amine instead of 4.7 ml of 40% aqueous methyl amine solution, to obtain 5.5 g of 3-O-(N,N-dimethyl) thiocarbamoyl-2-phenyl-1,3-propanediol carbamate: Yield 97%.

m.p.=114.5°–116° C.
$^1$H -NMR(CDCl$_3$, 200 MHz), ppm ($\delta$):
2.94–3.04(s,3H), 3.28–3.36(s,3H), 3.39–3.51(q,1H), 4.32–4.40(d,2H), 4.63–4.70(d,2H), 4.71–4.83(br,2H), 7.20–7.36(m,5H)

EXAMPLE IV
Preparation of 3-0-(N-isopropyl)thiocarbamoyl-2-phenyl-1,3-propanediol carbamate The procedure of Example II was repeated using 5.1 ml of isopropyl amino instead of 4.7 ml of 40% aqueous methyl amine solution, to obtain 5.3 g of 3-O-(N-isopropyl) thiocarbamoyl-2-phenyl-1,3-propanediol carbamate: Yield 90%.

$^1$H-NMR-(CDCl$_3$, 200 MHz), ppm (δ):
1.00–1.13(m,3H), 1.16–1.27(d,3H), 3.38–3.57(m,1H), 3.71–3.90(m,1H), 4.29–4.38(m,2H), 4.51–4.79(m,4H), 6.03–6.10(br,1H), 6.38–6.46(br,1H),7.18–7.39(m,5H)

EXAMPLE V
Preparation of 3-O-(N-cyclopropyl)thiocarbamoyl-2-phenyl-1,3-propanediol carbamate The procedure of Example II was repeated using 4.2 ml of cyclopropyl amine instead of 4.7 ml of 40% aqueous methyl amine solution, to obtain 5.3 g of 3-O-(N-cyclo propyl)thiocarbamoyl-2-phenyl1-1,3-propanediol carbamate: Yield 90%.

$^1$H-NMR(CDCl$_3$, 200 MHz),: ppm (δ):
0.46–0.88(m,4h), 2.52–2.66(m,1H), 2.86–2.98(m,3H), 3.34–3.58(m,1H), 4.28–4.44(d,2H), 4.57–4.69(d,2H), 4.70–4.80(br,2H), 6.37–6.43(br,1H), 6.76–6.84 (br,1H), 7.16–7.32(m,5H)

EXAMPLE VI
Preparation of 3-O-(N-octyl)thiocarbamoyl-2-phenyl-1,3-propanediol carbamate The procedure of Example II was repeated using 9.9 ml of octyl amine instead of 4.7 ml of 40% aqueous methyl amino solution, to obtain 7.2 g of 3-O-(N-octyl) thiocarbamoyl-2-phenyl-1,3-propanediol carbamate: Yield 98%.

$^1$H-NMR(CDCl$_3$, 200 MHz), ppm (δ):
0.81–1.65(m,15H), 3.02–3.17 (m,1H), 3.35–3.56(m,2H), 4.28–4.39(m,2H), 4.61–4.75(m,4H), 6.22–6.37(br,1H), 6.62–6.76(br,1H), 7.21–7.39(m,5H)

EXAMPLE VII

Preparation of 3-O-(N-piperidyl)thiocarbamoyl-2-phenyl-1,3-propanediol carbamate The procedure of Example II was repeated using 6.0 ml of piperidine instead of 4.7 ml of 40% aqueous methyl amine solution, to obtain 6.1 g. of 3-O-(N-piperidyl)thio carbamoyl-2-phenyl-1,3-propanediol carbamate: Yield 95%.

$^1$H-NMR(CDCl$_3$, 200 MHz), ppm (δ):
1.34–1.68(m,6H), 3.39–3.57(m,3H), 3.88–4.06(br,2H), 4.28–4.41(d,2H), 4.53–4.64(br,2H), 4.64–4.75(d,2H), 7.17–7.34 (m,5H)

EXAMPLE VIII
Preparation of 3-O-(N-ethoxycarbonyl)thiocarbamoyl-2-phenyl-1,3-propanediol carbamate 1000 ml flask equipped with thermometer and a reflux condenser was well dried and purged by flowing nitrogen gas into the inside thereof for 30 min to remove moisture and air which might be present therein. Then, 19.5 g of 2-phenyl-1,3-propanediol monocarbamate was dissolved in 300 ml of purified dichloromethane and placed in the flask. A homogeneous solution was made by stirring for 30 min.

While being maintained at room temperature, the homogeneous solution was slowly added with 15.7 g of ethoxy-carbonyl isothiocyanate using a syringe. Thereafter, temperature was slowly elevated to 40° C. at which the reaction was advanced with stirring. The progress of the reaction was monitored by thin layer chromatography and liquid chromatography. It took about 4 hours to determine the reaction termination.

Thereafter, the resulting reaction mixture was added with 200 ml of distilled water, for the purpose of solvent extraction. The organic layer thus obtained was dried over anhydrous magnesium sulfate and the solvent was completely evaporated by a rotary evaporator, to give yellow liquid. This residue was subjected to column chromatography (mobile phase, ethylacetate:n-hexane=1:1) to give 26.1 g of 3-O-(N-ethoxycarbonyl)thiocarbamoyl-2-phenyl-1,3-propanediol carbamate: Yield 80%.

$^1$H-NMR(CDCl$_3$, 200 MHz), ppm (δ)
1.15–1.26(t,3H), 3.38–3.50(m,1H), 4.11–4.20(q,2H), 4.35–4.44(d,2H), 4.0–4.81(m,2H), 4.95–5.07(br,2H), 7.15–7.42(m,5H), 8.80–8.88(br,1H).

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. 3-N-Substituted thiocarbamoyl-2-phenyl-1,3-propanediol carbamate, represented by the following structural formula I:

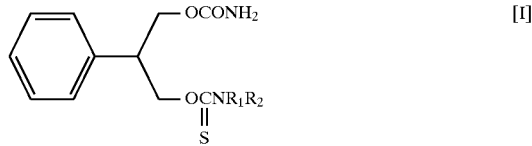

[I]

wherein $R_1$ and $R_2$ may be the same or different from each other and are independently selected from the group consisting of hydrogen, lower alkyl containing 1 to 8 carbon atoms, cyclic propyl and 5 to 7-membered aliphatic cyclic compounds and $R_1$ and $R_2$ together with the adjoining N-atom may form 4 to 7-membered aliphatic cyclic compounds optionally containing one or two additional nitrogen or oxygen atoms, excluding the instance where $R_1$ and $R_2$ are both hydrogen and the total number of carbon atoms or $R_1$ and $R_2$ ranges from 1 to 16.

2. A method for preparing 3-N-substituted thiocarbamoyl-2-phenyl-1,3-propanediol carbamate, represented by the following structural formula I:

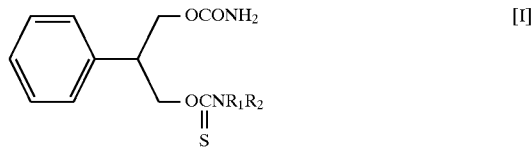

[I]

wherein $R_1$ and $R_2$ may be the same or different from each other and are independently selected from the group consisting of hydrogen, lower alkyl containing 1 to 8 carbon atoms, cyclic propyl and 5 to 7-membered aliphatic cyclic compounds and $R_1$ and $R_2$ together with the adjoining N-atom may form 4 to 7-membered aliphatic cyclic compounds optionally containing one or two additional nitrogen or oxygen atoms, excluding the instance where $R_1$ and $R_2$ are both hydrogen and the total number of carbon atoms of $R_1$ and $R_2$ ranges from 1 to 16, comprising the steps of:

reacting 2-phenyl-1,3-propanediol monocarbamate, represented by the following structural formula II:

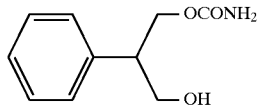

with sodium hydride and carbon disulfide in a solvent;

without separation thereof, treating the reaction solution with alkyl iodide, represented by the following structural formula IV:

$R_3I$ [IV]

where $R_3$ is a lower alkyl containing 1 to 3 carbon atoms, to synthesize 3-(alkyldithiocarbonyl)-2-phenyl- 1,3-propanediol carbamate, represented by the following structural formula III:

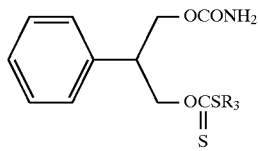

wherein $R_3$ is as defined above; and subjecting the carbamate of structural formula III to reaction with an amine, represented by the following formula V:

$HNR_1R_2$ [V]

wherein $R_1$ and $R_2$ is as defined above, in an ethereal solvent.

3. The method in accordance with claim 2, wherein $R_3$ is methyl.

4. The method in accordance with claim 2, wherein 2-phenyl-l,3-propanediol monocarbamate of structural formula II is used at an amount of about 0to 3.0 mole.

5. The method in accordance with claim 2, wherein sodium hydride and carbon disulfide each are used at an amount of about 1.0 to 2.0 equivalents.

6. The method in accordance with claim 2, wherein alkyl iodide of structural formula IV is used at an amount of about 1.0 to 2.5 equivalents.

7. The method in accordance with claim 2, wherein the reaction system is maintained at a temperature of −10° to 30° C.

8. The method in-accordance with claim 2, wherein the solvent used to synthesize 3-(alkyl dithiocarbonyl)-2-phenyl-1,3-propanediol carbamate of structural formula III is selected from the group consisting of amides such as dimethyl sulfoxide, and ethers.

9. The method in accordance with claim 8, wherein the solvent used to synthesize 3-(alkyldithiocarbonyl)-2-phenyl-1,3-propanediol carbamate of structural formula III is ethyl ether or tetrahydrofuran.

10. The method in accordance with claim 2, wherein the amine of structural formula V is used at an amount of about 1.0 to 5.0 equivalents.

11. 3-N-Substituted thiocarbamoyl-2-phenyl-1,3-propanediol carbamate, represented by the following structural formula I':

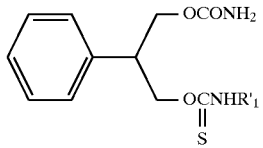

wherein $R'_1$ is an alkyloxy carbonyl containing 1 to 8 carbon atoms or an unsubstituted phenyl group, or a phenyl ring with a single chlorine or fluorine atom in the ortho-, meta-, or para-position.

12. The method for preparing 3-N-substituted carbamoyl-2-phenyl-1,3-propanediol, represented by the following structural formula I':

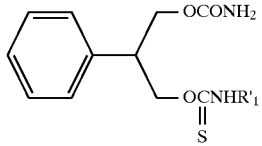

wherein $R'_1$ is an alkyloxycarbonyl containing 1 to 8 carbon atoms or an unsubstituted phenyl group, or a phenyl ring with a single chlorine or fluorine atom in the ortho-, meta-, or para-position, comprising the reaction of 2-phenyl-1,3-propanediol monocarbamate, represented by the following structural formula II:

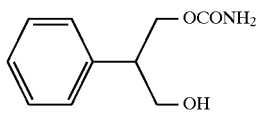

with alkyloxyisothiocyanate, represented by the following structural formula VI:

$R'_1 NCS$ [VI]

wherein $R'_1$ is as defined above, in a solvent.

13. The method in accordance with claim 12, wherein 2-phenyl-1,3-propanediol monocarbamate of structural formula II is used at an amount of about.0.1 to 3.0 moles with the amount of the alkyloxy isothiocyanate ranging from about 1.0.to 2.0 equivalents.

14. The method in accordance with claim 12, wherein the reaction system is maintained at a temperature of 30° to 110° C.

15. The method in accordance with claim 12, wherein the solvent is selected from the group consisting of halogenated hydrocarbons and aromatic hydrocarbons.

16. The method in accordance with claim 15, wherein the solvent is dichloromethane or chloroform.

17. A method in accordance with claim 8, wherein the amide is N,N-dimethylformamide.

18. A method in accordance with claim 8, wherein the sulfoxide is dimethyl sulfoxide.

19. A method in accordance with claim 8, wherein the ether is selected from ethyl ether and tetrahydrofuran.

20. A method in accordance with claim 15, wherein the halogenated hydrocarbon is selected from dichloromethane and chloroform.

21. A method in accordance with claim 15, wherein the ether is selected from ethyl ether and tetrahydrofuran.

22. A method in accordance with claim 15, wherein the aromatic hydrocarbon is benzene.

* * * * *